United States Patent [19]

Galbenu

[11] Patent Number: 5,535,737
[45] Date of Patent: Jul. 16, 1996

[54] ANESTHETIC VAPORIZERS

[75] Inventor: Lucian Galbenu, Keighley, England

[73] Assignee: The BOC Group, Inc., Windlesham, England

[21] Appl. No.: 340,553

[22] Filed: Nov. 16, 1994

[30] Foreign Application Priority Data

Nov. 16, 1993 [GB] United Kingdom ............. 9323645

[51] Int. Cl.$^6$ .................................................. A61M 16/00
[52] U.S. Cl. ........................... 128/203.14; 128/203.12; 128/203.25; 128/203.26; 128/203.27; 128/204.14; 128/204.21
[58] Field of Search ................... 128/204.21, 204.22, 128/204.24, 203.25, 204.13, 204.14, 203.12, 203.13, 203.14, 203.15, 203.25, 203.26, 203.27

[56] References Cited

U.S. PATENT DOCUMENTS

| | | | |
|---|---|---|---|
| 3,593,710 | 7/1971 | Eichelman et al. | 128/203.25 |
| 3,739,799 | 6/1973 | Bickford et al. | 128/203.12 |
| 3,741,208 | 6/1973 | Jonsson et al. | 128/204.21 |
| 3,923,056 | 12/1975 | Bingmann et al. | 128/204.21 |

FOREIGN PATENT DOCUMENTS

| | | | |
|---|---|---|---|
| 4105971 | 2/1991 | Germany | 128/203.25 |
| 2148721 | 6/1985 | United Kingdom | 128/203.12 |

*Primary Examiner*—Ren Yan
*Assistant Examiner*—V. Srivastava
*Attorney, Agent, or Firm*—Roger M. Rathbun; Larry R. Cassett; R. Hain Swope

[57] ABSTRACT

An anesthetic vaporizer 1 includes an inlet 2 for carrier gas, an outlet 4 for carrier gas and anesthetic agent, a first passage 6 interconnecting the inlet to the outlet and a first fixed flow restrictor 8 located in the passage 6. A second passage 56 extends between a vaporizing chamber and the outlet 4 and located therein is a second fixed flow restrictor 54 and also a solenoid valve 58. A first pressure transducer 50 generates an electrical signal corresponding to the pressure differential P1 across the restrictor 8; and a second pressure transducer 52 generates an electrical signal corresponding to the pressure differential P2 between the passages 6, 56. A controller responsive to said electrical signals from the pressure transducers 50, 52 transmits an electrical signal to the valve 58 for controlling the flow of gaseous anesthetic agent through the passage 56 such that $P2 = P1 \times \text{constant}$.

4 Claims, 2 Drawing Sheets

ANESTHETIC VAPORIZERS

FIELD OF THE INVENTION

The present invention relates to anesthetic vaporizers.

There is described in UK Patent Publication No. 2239807 an anesthetic vaporizer for use in administering an anesthetic agent having a low boiling point at atmospheric pressure in the order of 20° C. to 25° C. The vaporizer disclosed in this document includes a first passage which extends between an inlet for a carrier gas and an outlet for carrier gas and a preselected concentration of gaseous anesthetic agent. Located in the first passage between the inlet and the outlet is a laminar flow fixed restrictor. A second passage extends between the first passage at a location upstream of the fixed restrictor and one chamber of balance regulator. The balance regulator includes a second chamber separated from the first chamber by a diaphragm to which is connected for movement therewith a valve head. The valve head cooperates with a valve seat to control the flow of gaseous anesthetic agent contained in a vaporizing chamber. From the second chamber there extends a third passage which communicates with the first passage downstream of the fixed restrictor. A laminar flow variable restrictor (rotary valve) is located in the third passage.

In use, energy is supplied to the vaporizer which converts the anesthetic agent from a liquid to a gaseous state within the vaporizing chamber. Carrier gas then enters the inlet and continues along the first passage through the fixed restrictor towards the outlet. The pressure upstream of the fixed restrictor is dependent upon the flow rate of carrier gas entering the inlet. The pressure in the first chamber of the regulator is the same as that upstream of the fixed restrictor because of the second passage. This causes the diaphragm to move taking with it the valve head. The valve head will thus separate from its cooperating valve seat thereby enabling gaseous anesthetic agent to leave the vaporizing chamber and pass through the second chamber of the regulator into the third passage until the pressure in the third passage is the same as that in the first chamber. The pressure in the first passage upstream of the fixed restrictor and the pressure in the third passage upstream of the variable restrictor are the same.

For any position of the variable restrictor the flow rate of gaseous anesthetic agent will depend on that pressure and hence the carrier gas flow rate at the inlet. This ensures that the flow of an anesthetic agent rises when the carrier gas flow rate rises and vice versa and hence the percentage concentration by volume of the anesthetic agent in the gas delivered to the patient remains constant.

Although highly successful in delivering 2-(difluoromethoxy)-1,1,1,2-tetraflouro ethane which has a boiling point at atmospheric pressure of between 20° C. and 25° C.; it has been found that with this known anesthetic vaporizer it is occasionally difficult to avoid gas leakage around the variable restrictor.

It is an aim of the present invention to provide an anesthetic vaporizer capable of delivering to a patient a predetermined concentration of an anesthetic agent having a boiling point at normal atmospheric pressure of approximately 20° C. which does not include a variable restrictor.

According to the present invention, an anesthetic vaporizer comprises an inlet for carrier gas, an outlet for carrier gas and gaseous anesthetic agent for delivery to a patient, a first passage extending between the inlet and the outlet in which is located a first fixed flow restrictor, a first pressure transducer for transmitting to a controller a first electrical signal corresponding to the pressure differential P1 across the first fixed flow restrictor, a second passage extending from a vaporizing chamber containing anesthetic agent to the outlet and having located therein a second fixed flow restrictor, a second pressure transducer connected between the first and second passages upstream of their respective fixed flow restrictors for transmitting to the controller a second electrical signal corresponding to the pressure differential P2 between the passages, the controller, in use, transmitting an electrical signal to a solenoid valve located in the second passage for controlling the flow of gaseous anesthetic agent therethrough such that P2=P1×constant.

A linear potentiometer may be provided for changing the value of the constant and hence the percentage concentration of the anesthetic agent in the gas delivered to the patient.

An embodiment of the invention will now be described by way of example reference being made to the Figures of the accompanying diagrammatic drawings in which:

DETAILED DESCRIPTION

Figure 1:
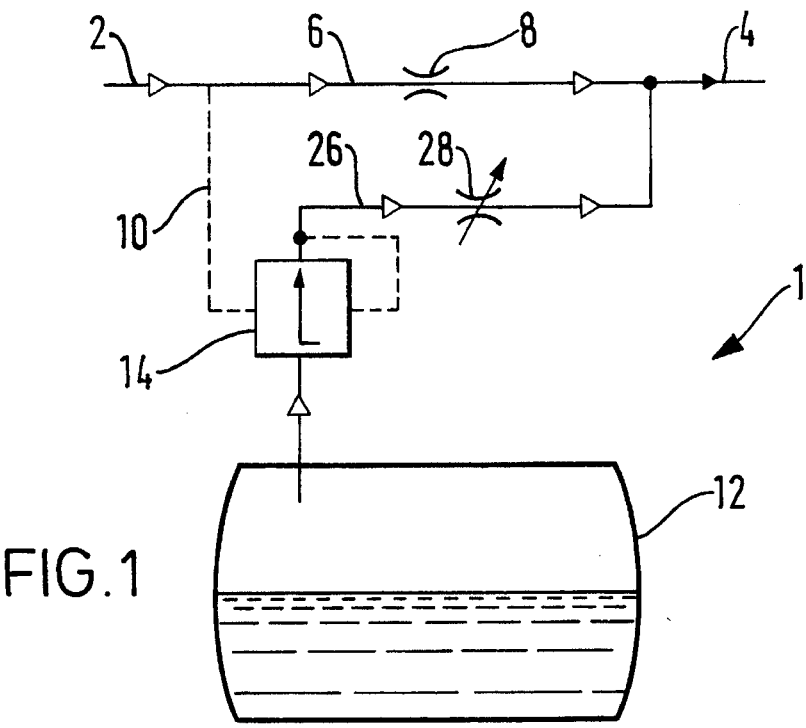
FIG. 1 is a diagrammatic sketch of an anesthetic vaporizer as described in UK Patent Application Publication No. 2239807.
Figure 2:
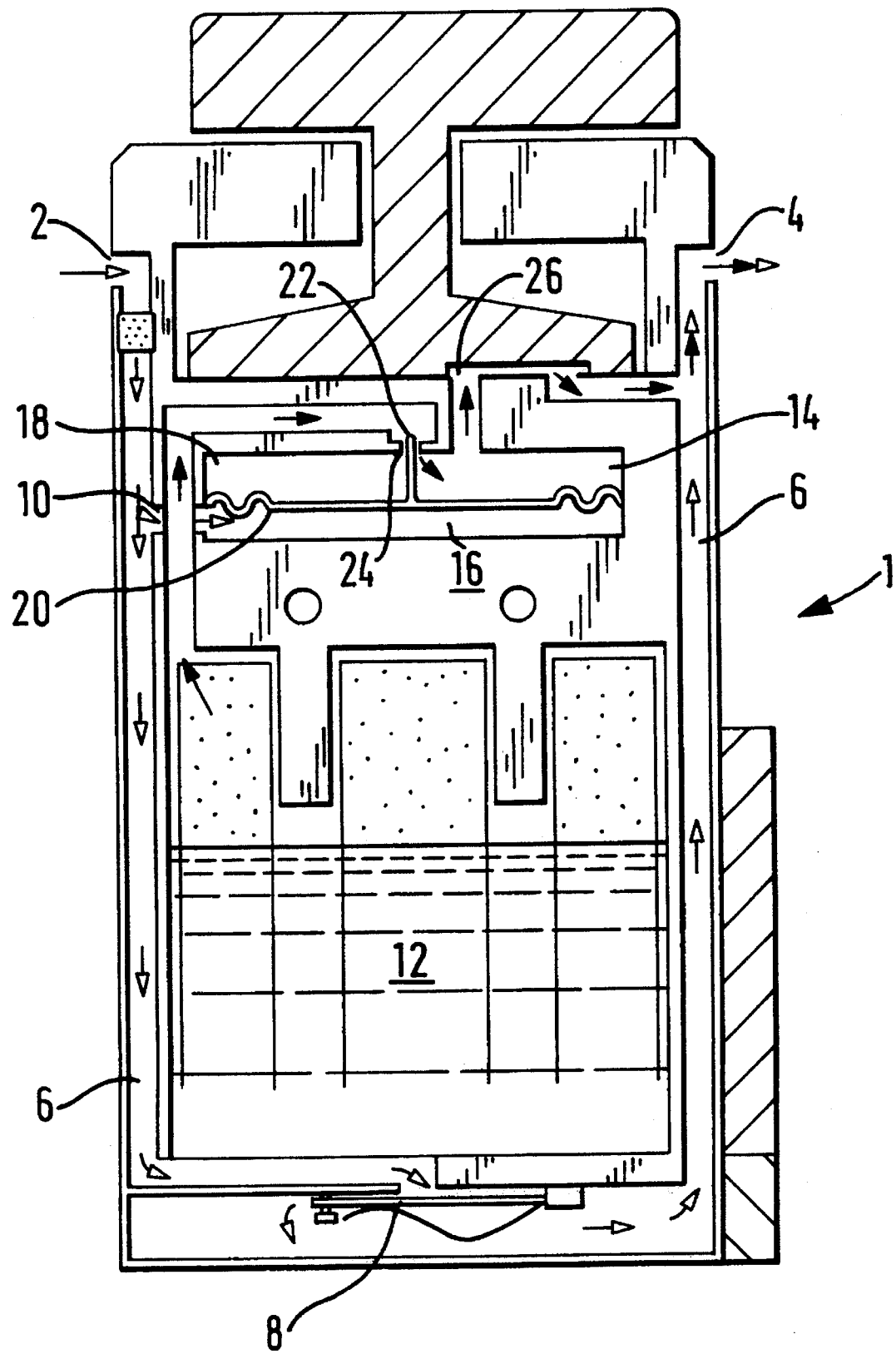
FIG. 2 is a side view partly in cross-section of the anesthetic vaporizer of FIG. 1.

Referring first to FIGS. 1 and 2, an anesthetic vaporizer 1 has an inlet 2 for carrier gas and an outlet 4 for carrier gas and gaseous anesthetic agent. Extending between the inlet 2 and the outlet 4 is a passage 6 in which is located a laminar flow by-pass fixed restrictor 8.

Extending from the passage 6 at a location upstream of the fixed flow restrictor 8 is a second passage 10 communicating with a first chamber 16 of a balance regulator 14. The balance regulator 14 includes a second chamber 18 which is separated from the first chamber 16 by a diaphragm 20. Connected to the diaphragm 20 for movement therewith is a valve 22 head which co-operates with a valve seat 24. The valve head 22 and valve seat 24 control the flow of gaseous anesthetic agent contained in a vaporizing chamber 12. Extending from the second chamber 18 is a passage 26 which extends to the passage 6 at a location downstream of the fixed flow restrictor 8. A laminar flow variable control valve 28 is located in the passage 26.

As explained in UK Patent Application Publication No. 2239807, in use, anesthetic agent contained within the vaporizing chamber 12 is vaporized and subsequently carrier gas enters inlet 2 and continues along passage 6 through the fixed flow restrictor 8 towards the outlet 4. The pressure upstream of the fixed flow restrictor 8 is dependent on the flow rate of carrier gas entering the inlet 2. The pressure in the first chamber 16 of the balance regulator 14 is the same as that upstream of restrictor 8 because of the second passage 10. This causes the diaphragm 20 to move upwards (as shown) taking with it the valve head 22. The valve head 22 will thus separate from the valve seat 24 thereby enabling gaseous anesthetic agent to leave the vaporizing chamber 12 and pass through the second chamber 18 into the passage 26 until the pressure in the passage 26 is the same as that in the chamber 16. The pressure in passage 6 upstream of the fixed restrictor 8 and passage 26 upstream of the control valve 28 are the same. For any position of the control valve 28 the flow rate of gaseous anesthetic agent will depend on that pressure and hence the carrier gas flow rate in the inlet 2. This ensures that the flow rate of anesthetic agent rises when the carrier gas flow rate rises and vice versa and hence the percentage concentration by volume of the anesthetic agent in the gas delivered to the patient remains constant.

Figure 3:
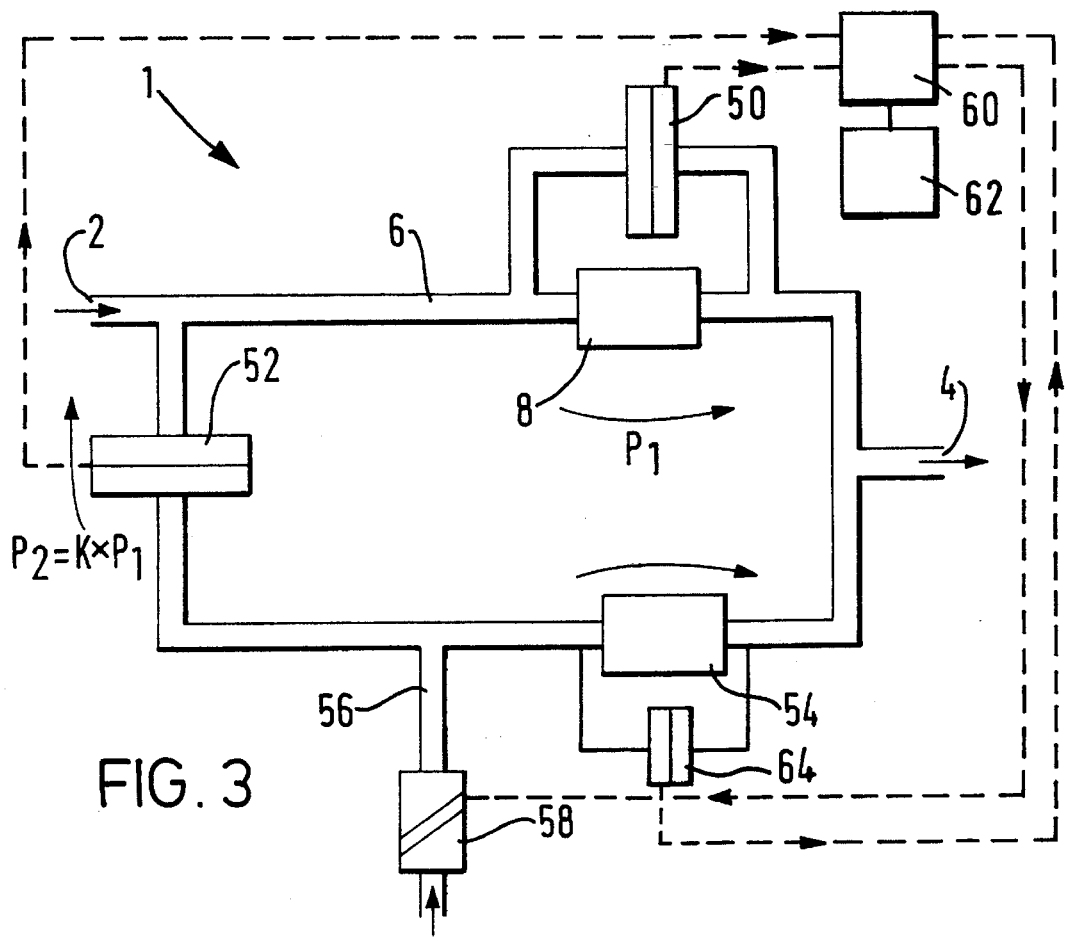
FIG. 3 is a diagrammatic sketch of a modification of the anesthetic vaporizer portrayed in FIGS. 1 and 2 which modification incorporates the invention as defined in the appendant claims.

Referring now to FIG. 3, where like reference numerals denote the same or similar structures.

The modified anesthetic vaporizer 1 has an inlet 2 for carrier gas and an outlet 4 for carrier gas and gaseous anesthetic agent. Extending between the inlet 2 and the outlet 4 is a passage 6 in which is located a laminar flow fixed flow restrictor 8 and in parallel with the fixed flow restrictor 8 is a first pressure transducer 50.

A second passage 56 extends from the interior of a vaporizing chamber (not shown) to the outlet 4. Located in the passage 56 is a second laminar flow fixed flow restrictor 54 and between said second fixed flow restrictor 54 and the vaporizing chamber, an electronically operated proportional solenoid valve 58. A second pressure transducer 52 has an upper (as shown) end communicating with the passage 6 and a lower (as shown) end communicating with the passage 56.

As shown the second passage 56 reconnects with the first passage 6 at a location downstream of the fixed flow restrictor 8 and immediately upstream of the outlet 4.

In use, energy supplied by heaters (not shown) adjacent the vaporizing chamber converts liquid anesthetic agent in said vaporizing chamber to a gaseous state. Carrier gas then enters the inlet 2 and most will proceed along the passage 6 through the fixed flow restrictor 8 towards the outlet 4. The pressure differential P1 across the fixed flow restrictor 8 will be sensed by the pressure transducer 50 and an electrical/electronic signal generated which is fed to a control unit (not shown).

Simultaneously, the pressure transducer 52 will send a signal P2 which is fed to the control unit 60. On the basis of the signals received from the pressure transducers 50, 52 a signal from the control unit 60 will be sent to the control valve 58 to apply a pressure differential across the pressure transducer 52 of P2=K×P1 where K is a constant that is set for a required concentration of agent output from the vaporizer. It will be apparent that to change the agent concentration the value of K is altered, for example, by means of a linear potentiometer 62 calibrated in percentage output of agent concentration.

As will be appreciated the second pressure transducer 52 does not allow the flow of gas between the passage 6 (carrier gas) and the passage 56 (100% agent vapor). The solenoid valve 58 however is controlled to keep a differential pressure between the carrier gas in passage 6 and the agent vapor in passage 56 according to the formula P2=K×P1.

The agent vapor will flow through the second fixed flow restrictor 54 and mix with the carrier gas flowing through the passage 6 prior to leaving the vaporizer 1 via the outlet 4.

An advantage of the above described modification is that the output concentration of gaseous anesthetic agent is not dependent on carrier gas flow rate and for a preset value of K will give the same output concentration of agent for any variety of flow rates of carrier gas.

Furthermore, since both the flow restrictors 8, 54 are fixed the likelihood of gas leakage is substantially reduced.

In a modification, a further pressure transducer 64 can be used to monitor the pressure differential across the fixed flow restrictor 54 which should be P3=P1+P2=P1 (K+1). The control unit will compare the voltage from this further pressure transducer 64 with the voltage from the pressure transducer 50 and when multiplying by K+1 if the two voltages are not equal then an alarm can be activated.

I claim:

1. An anesthetic vaporizer comprising an inlet for carrier gas, an outlet for carrier gas and gaseous anesthetic agent for delivery to a patient, a controller a first passage extending between the inlet and the outlet in which is located a first fixed flow restrictor, a first pressure transducer for transmitting to said controller a first electrical signal corresponding to the pressure differential P1 across the first fixed flow restrictor, a vaporizing chamber containing anesthetic agent, a second passage extending from said vaporizing chamber to the outlet and having located therein a second fixed flow restrictor, a second pressure transducer connected between the first and second passages upstream of their respective fixed flow restrictors for transmitting to the controller a second electrical signal corresponding to the pressure differential P2 between the passages, a solenoid valve located in the second passage for controlling the flow of gaseous anesthetic agent therethrough such that P=P1×constant, said controller, in use, transmitting an electrical signal to said solenoid valve.

2. An anesthetic vaporizer as claimed in claim 1, in which a linear potentiometer is provided for changing the value of the constant.

3. An anesthetic vaporizer as claimed in claim 1, in which a third pressure transducer is provided for measuring the pressure differential across the second fixed flow restrictor.

4. An anesthetic vaporizer as claimed in claim 1, in which the first and second fixed flow restrictors are substantially laminar flow devices over their operating flow ranges.

* * * * *